United States Patent
Bevinakatti et al.

(10) Patent No.: US 8,097,564 B2
(45) Date of Patent: Jan. 17, 2012

(54) SURFACTANT COMPOUNDS

(75) Inventors: Hanamanthsa Shankarsa Bevinakatti, Ingleby Barwick (GB); Alan Geoffrey Waite, Darlington (GB)

(73) Assignee: Croda International PLC, Goole, North Humberside (GB)

( * ) Notice: Subject to any disclaimer, the term of this patent is extended or adjusted under 35 U.S.C. 154(b) by 0 days.

(21) Appl. No.: 12/312,586

(22) PCT Filed: Nov. 14, 2007

(86) PCT No.: PCT/GB2007/004337
§ 371 (c)(1),
(2), (4) Date: Sep. 8, 2010

(87) PCT Pub. No.: WO2008/059234
PCT Pub. Date: May 22, 2008

(65) Prior Publication Data
US 2010/0331191 A1 Dec. 30, 2010

(30) Foreign Application Priority Data
Nov. 17, 2006 (GB) .................................. 0622947.0

(51) Int. Cl.
*A01N 25/00* (2006.01)
(52) U.S. Cl. ...................... 504/363; 514/785; 528/295.5; 516/135; 507/117; 524/827; 149/1; 424/59; 510/276
(58) Field of Classification Search .................. 504/363; 514/785; 528/295.5; 516/135; 507/117; 524/827; 149/1; 424/59; 510/276
See application file for complete search history.

(56) References Cited

U.S. PATENT DOCUMENTS
3,255,108 A  6/1966  Wiese
3,255,180 A *  6/1966  Hoeksema .................... 536/17.2

FOREIGN PATENT DOCUMENTS
WO  WO 96/25384  8/1996
WO  WO 9625384 A1 *  8/1996

OTHER PUBLICATIONS

ASE CA [Online] Chemical Abstracts Service, Columbus,.Ohio, US; Makhkamov, R. R.: Preparation and surface-active properties of polyfunctional derivatives of heptylenesuccinic acid': XP002468598 retrieved from STN Database access, ion No. 2000:22187.*
International Search Report dated May 29, 2008 for PCT/GB2007/004337.
Makhkamov, R. "Preparation and surface-active properties of polyfunctional derivatives of heptylenesuccinic acid" [abstract from Chemical Abstracts Service, STN Database Accession No. 2000:22187] *O'zbekiston Kimyo Jumafi* (4) 38-41, ISSN: 0042-1707 (1999).

* cited by examiner

*Primary Examiner* — Deborah D Carr
(74) *Attorney, Agent, or Firm* — Jones Day

(57) ABSTRACT

Oligoesters including residues of alk(en)yl succinic anhydrides and polyols having at least 3 OH groups, optionally further esterified with fatty acid residues are surfactants which can be used for emulsifiers or similar uses. The surfactants are usually made from $C_8$ to $C_{30}$ alk(en)yl succinic anhydride and polyols having at least 4 hydroxyl groups and are particularly of the formula (I): $R^1$—[$OR^2O(O)C.C(HR^3).(HR^4)C.C(O)]_m$—$R^5$ (I), where $R^1$, $R^2$, $R^3$, $R^4$, $R^5$, $R^6$, $R^7$ and m have defined meanings. The surfactants are useful as emulsifiers, particularly oil in water emulsifiers.

30 Claims, No Drawings

SURFACTANT COMPOUNDS

CROSS REFERENCE TO RELATED APPLICATION

This application is the National Phase application of International Application No. PCT/GB2007/004337, filed Nov. 14, 2007, which designates the United States and was published in English. This application, in its entirety, is incorporated herein by reference.

This invention relates to surfactant compounds which include oligo- or poly-meric esters made up of polyhydroxy hydrocarbyl, particularly saccharide, residues, and dicarboxylic acid residues derived from alkyl or alkenyl substituted succinic acid(s) and to the use of such compounds as surfactants.

For effective surfactancy in water based systems, e.g. oil in water emulsions, or dispersing solids in water, it is usually desirable to use surfactants which are relatively hydrophilic, and are typically moderately water soluble. Such surfactants usually have a high HLB (Hydrophile/Lipophile Balance), typically greater than 7 and commonly in the range 8 to 18. Conventionally this has been achieved by using alcohol ethoxylates having relatively long polyoxyethylene chains, typically including at least 10 and sometimes up to about 100 EO groups, for alcohols having $C_{12}$ to $C_{18}$ chains, or by using fatty acid esters, usually mainly mono-esters of sugars such as sucrose.

Correspondingly for effective surfactancy in oil based systems it is desirable to use surfactants that are relatively hydrophobic, usually oil soluble and often water insoluble, typically having a low HLB e.g. less than 7 and commonly in the range 4 to 6.

The present invention is based on our finding that certain polyesters of polyols and substituted, particularly alkyl or alkenyl substituted, dicarboxylic succinic anhydrides, acids or derivatives give oligomers or polymers which optionally can be further esterified typically with monocarboxylic acids, giving compounds which have surfactant activity for example as emulsifiers. For convenience the polyester products may be simply referred to as oligoesters or oligomers.

The present invention accordingly provides an oligoester surfactant compound which includes residues of an alk(en)yl succinic anhydride, acid or reactive derivative; of a polyol having at least 3 OH groups; and, optionally, of a fatty acid. In particular, the compounds of the invention are oligoester surfactant compounds which are reaction products of at least one alk(en)yl succinic anhydride, acid or reactive derivative; at least one polyol having at least 3 OH groups; and optionally a fatty monocarboxylic acid or a reactive derivative.

Typically, the compounds of the invention are made using:
i) a $C_6$ to $C_{30}$ alkenyl succinic acid or anhydride; and/or
ii) a polyol having from 4 to 6 carbon atoms and at least 4 hydroxyl groups, especially sorbitol.

Typically the compounds of the invention are made using polyols that have at least 4 OH groups. After the esterification reaction, the products will usually have an average of at least 1, particularly at least 1.5, desirably at least 2, and most usually at least 3, free hydroxyl groups per polyol residue. The molar ratio of the polyol to the alk(en)yl succinic anhydride, acid or reactive derivative used as starting materials is typically from 1:0.5 to 1:1.5, particularly from 1:0.6 to 1:1.3, especially from 1:0.6 to 1:1, with corresponding ratios of the respective residues in the oligoester surfactant products.

The compounds of the invention include polyol alk(en)yl succinic anhydride oligomers and fatty acid esters of such oligomers and the invention includes the following types of compound.

In particular, the compounds of the invention are of the formula (I)

where
$R^1$ is H or a group $R^6(O)C—$;
each $R^2$ is independently a $C_3$ to $C_{10}$, desirably a $C_4$ to $C_8$ and usually a $C_5$ to $C_7$, hydrocarbyl group having at least one hydroxyl group which is either substituent free; esterified with a fatty acid residue of the formula $R^{6'}(O)C—$, where $R^{6'}$ is independently as defined for $R^6$, or esterified with an alk(en)yl succinic terminated oligoester group of the formula: $—[O(O)C.C(HR^{3'}).(HR^{4'})C.C(O)OR^{2'}]_{m'}—R^{1'}$, where $R^{1'}$, $R^{2'}$, $R^{3'}$, $R^{4'}$, and m' are independently as defined for $R^1$, $R^2$, $R^{3'}$, $R^{4'}$, and m' respectively;
independently for each pair of groups $R^3$ and $R^4$ on adjacent carbon atoms one is a $C_6$ to $C_{30}$ alkenyl or alkyl group and the other is hydrogen;
$R^5$ is —OH, —OM where M is a salt forming metal, an amine or ammonium group, a group —$OR^7$, or a group —$OR^2O—R^7$;
$R^6$ is a $C_1$ to $C_{21}$ more usually a $C_7$ to $C_{21}$ aliphatic hydrocarbyl group;
$R^7$ is H or a group —$C(O)R^6$ where $R^6$ is independently as defined above; and
m is from 1 to 20, particularly from 1 to 10, desirably from 1.5 to 8, and especially from 2 to 5.

The oligoesters of the formula (I) will typically be a mixture of materials with hydroxyl and carboxyl ends. However, as there is usually a substantial molar excess of hydroxyl groups over carboxyl groups in the starting materials the compounds of the invention will usually be at least mainly hydroxyl ended. Thus, within the general formula (I), the invention particularly includes the following groups of compounds:
a) polyol ended binary co-oligomers of the polyol and alk(en)yl succinic anhydride of the formula (Ia):

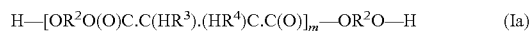

where $R^2$, $R^3$, $R^4$ and m are as defined in formula (I).
b) fatty acid esters of the formula (Ib):

where
each $R^3$, $R^4$ and m is independently as defined in formula (I);
each $R^{1b}$ and each $R^{5b}$ is independently —H, or a group —$C(O)R^6$;
each $R^{2b}$ is independently a group $R^2$ as defined in formula (I), or such a group esterified with one or more groups —$C(O)R^6$; where each $R^6$ is independently as defined in formula (I); and
n is 0 or 1, particularly 1 [when n is 1, the compounds of the formula (Ib) can be considered as esters of compounds of the formula (Ia)];
such that the compound includes an average of at least 0.1, usually at least 2, typically at least 0.25 and usually up to 1, more usually up to 0.8 and typically up to 0.5, group —$C(O)R^6$ and an average of at least one, usually at least 1.5 and desirably at least 2 OH group(s).

As noted above, the compounds of the invention, and particularly of the formula (Ia), are polyol ended and thus include an "extra" polyol residue —OR²O— and as these residues are the main source of hydrophilicity in the molecule it is likely that such compounds will be intended to be relatively hydrophilic, commonly water soluble and particularly having an HLB value of from 8 to 18.

Esters of the formula (Ib) include additional hydrophobicity derived from the presence of the carboxylate group(s)—COR₆, either because it esterifies a hydroxyl group (which would otherwise contribute hydrophilicity) or because the carboxylate group includes a fatty chain, $R^6$ e.g. a $C_7$ to $C_{21}$ group, or both. Such compounds will usually be intended to be relatively hydrophobic, commonly water insoluble, often oil soluble and particularly having an HLB value of from 4 to 6.

The term "alk(en)yl" in relation to the substituent on the succinic moiety in formula (I) and elsewhere is used to briefly refer to both alkenyl and alkyl groups. Alkenyl succinic anhydrides are well known compounds e.g. used as paper sizing materials, and are typically made by reaction of maleic anhydride and a terminal olefin corresponding to the desired length of the side chain. The corresponding acids can be made by hydrolysis of the anhydride e.g. with aqueous alkali. The corresponding alkyl substituted compounds can be made by catalytic hydrogenation of the alkenyl substituted materials, usually on the anhydride and, if desired, followed by hydrolysis. The abbreviation "ASA" is used to refer to alkenyl or alkyl succinic anhydrides and by extension to the corresponding acids and their residues in polymers. ASAs are commonly described by the length of the substituent chain e.g. "$C_{12}$ ASA" or "dodecenyl succinic anhydride" refer to a succinic anhydride or the corresponding acid or group residue (as the case may be) with a $C_{12}$ alk(en)yl substituent, even though the overall molecule has a total of 16 carbon atoms.

Formula (I) shows the oligoesters as linear, but this is probably a simplification in that, particularly if the oligoesters are made by reaction of an alk(en)yl succinic anhydride with the precursor polyol, reaction of the anhydride is likely at both primary and secondary OH groups in the polyol leading to a "kinked" chain (a "truly" linear chain would usually have chain extending ester links at primary hydroxyl groups at the ends of the polyol molecule) and there may be chain forming esterification at more than 2 of the polyol OH groups which may lead to branching of the oligomeric chain.

The hydrocarbyl group $R^2$ can be considered as the residue of a corresponding polyol HO—$R^2$—OH (II) after removing the two hydroxyl groups linking it into the oligoester chain. $R^2$ is desirably an aliphatic hydrocarbyl group, which will usually be saturated, having from 3 to 10 and particularly 4 to 8, and especially 6, carbon atoms and it will desirably be linear. The residue $R^2$ includes at least 1, usually at least 2, more usually at least 3 and desirably from 3 to 6, particularly 3 or 4, especially 4, hydroxyl groups which will usually be mostly secondary hydroxyl groups.

Particularly desirably, $R^2$ is of the formula: —(CH2)$_{p1}$(CHOH)$_{p2}$(CH2)$_{p3}$— where p1 and p3 are each independently from 1 to 3, desirably 1, and p2 is from 1 to 6, more usually from 2 to 4, particularly 3 or 4. Such polyols are commonly described as sugar alcohols and include glycerol, but more desirably $C_4$ polyols, such as threitol and erythritol, $C_5$ polyols, such as ribitol, arabitol and xylitol and $C_6$ polyols, such as sorbitol and inositol. The $C_4$ to $C_6$ polyols are commonly the reduced or hydrogenated forms of the corresponding tetrose, pentose and hexose sugars respectively. Such polyols have two primary hydroxyl groups and correspondingly 1 to 4, more particularly 2 to 4, especially 3 or 4, secondary hydroxyl groups. Usually it will be desirable to have a relatively large number of free hydroxyl groups to maximise the hydrophilic contribution of this part of the molecule, however, if desired the number of free hydroxyl groups can be less than the maximum possible e.g. 4 with sorbitol, by reacting the groups e.g. by esterification, or by using modified polyols e.g. by forming sorbitan by the anhydridisation of sorbitol, typically in situ in the esterification reaction. The polyols residues $R^2$ may be or include groups derived from disaccharides, in particular disaccharide sugar alcohols such as maltitol, isomaltitol, isomalt (a mixture of 1,6-glucopyranosyl-D-sorbitol and 1,1-glucopyranosyl-D-mannitol) and lactitol; such groups may be advantageous in providing further hydrophilicity to the oligoesters. Such disaccharide derivatives may be considered as a hexitol polyol substituted with a monosaccharide residue.

One or more of the polyol residues $R^2$ may include substitution on hydroxyl groups (other than those esterified to link it into the oligoester chain), in particular by acyl groups, as in formula (Ib), or of ASA carboxyl terminated oligoester residues, as when the oligoester chain is branched. Apart from this the polyol residues $R^2$ will not generally be substituted with other groups, particularly groups which reduce the hydrophilicity of the oligoesters.

It is possible to include relatively small proportions of polyol residues which have no free hydroxyl groups e.g. as derived from ethylene, diethylene, triethylene or propylene glycols or by reacting the polyol so that it only has 2 hydroxyl groups e.g. as in iso-sorbide derived by di-anhydridisation of sorbitol. However, as it is generally desirable to use this part of the molecule to provide hydrophilicity, the proportion of such residues will generally be low, typically an average of not more than 25 mol %, more usually not more than 10 mol %, and desirably not more than 5 mol % of the polyol plus diol residues in the molecule. Such glycol type polyols can be incorporated as pre-formed hydroxyl ended oligomers of the polyol and a diacid.

The group OC.(HR³)C.C(HR⁴).CO can be considered as the residue of the corresponding dicarboxylic acid HOOC.(HR³)C.C(HR⁴).COOH (III), and the dicarboxylic acid (III) or the corresponding anhydride, or other reactive derivative e.g. a $C_1$ to $C_4$ alkyl diester, will usually be the synthetic precursor providing the group OC.(HR³)C.C(HR⁴).CO to the compounds of the invention. The alk(en)yl group $R^3$ or $R^4$ or can be saturated or unsaturated, and is usually linear. Commonly the alk(en)yl group $R^3$ or $R^4$ is a $C_6$ to $C_{30}$, more usually a $C_8$ to $C_{20}$, alk(en)yl group. Generally, the longer the alk(en)yl chain in the substituted succinic residue, the more hydrophobic the product.

It is possible to include residues from other diacids in particular residues of dicarboxylic acids of the formula HOOC—$R^8$—COOH (IV) in which $R^8$ is a saturated or unsaturated, linear or branched, desirably aliphatic, group, typically an alkylene or alkenylene group, and may be cyclic though it is desirably open chain. Commonly $R^8$ is a group: —(CH₂)$_q$—, where q is from 1 to 10, usually from 2 to 10, particularly from 2 to 8, more particularly from 2 to 6. Because mixtures of different dicarboxylic acids (or reactive derivatives) may be used to make materials used in practice, q may appear to be non integral, because it will be an average. The group $R^8$ is usually unsubstituted, but may be substituted. Suitable diacids include succinic and maleic acids, which may be provided for reaction as the corresponding anhydrides. As such diacids will generally be less hydrophobic than the alk(en)yl succinic groups, they may be used to vary (modestly increase) the HLB of the product. The proportion of such residues may vary widely e.g. from 5 to 95 mol % with correspondingly from 95 to 5 mol % ASA residues. The use of less than 5 mol % diacid residues is likely to give only a very small change in the hydrophilicity of the product and the use of less than 5 mol % ASA residues will give a product very similar to one with no ASA residues at all. Within this broad range the proportion of non-ASA diacid will typically be from 10 to 90 mol %, more usually from 20 to 80 mol %. Such diacids may be incorporated as, usually polyol ended, pre formed oligomers of a polyol and a diacid.

The group $R^5$ is the end group of a chain terminating dicarboxylic acid group and is a free carboxylic hydroxyl group or a salt group of the carboxylate function. In this context, M is a salt forming metal, an amine or ammonium group. Where M is metal it is particularly an alkali metal e.g. sodium or potassium atom; where M is amine it is particularly mono-, di- or tri-, alkyl or hydroxyalkyl amine, typically containing in total from 1 to 12 carbon atoms; and where M is ammonium, it may be unsubstituted or substituted e.g. with 1 to 4 alkyl or hydroxyalkyl groups, typically containing in total from 1 to 16 carbon atoms.

The $C_1$ to $C_{21}$, particularly $C_7$ to $C_{21}$, aliphatic hydrocarbyl group $R^6$ can be considered as the residue of the corresponding carboxylic, particularly fatty, acid: $R^6COOH$ (V) and within the compounds of the invention usually appears as part of a carboxyl residue $R^6(O)C—$. The group $R^6(O)C—$ can be used simply as a hydroxyl group blocker, when it will typically be a short chain carboxylic acid residue particularly acetyl or propionyl, or, and more usually, it will be present to provide additional hydrophobic group(s), in which case it will typically be a $C_7$ to $C_{21}$, particularly a $C_7$ to $C_{17}$, alkyl, alkenyl or alkadienyl group. Each group $R^6$ is defined independently within the overall range and is particularly an alkyl, alkenyl or alkadienyl group. It may be desirable to use a mixture of compounds having different groups $R^6$, e.g. as derived from naturally occurring fats and oils or as iso-stearic acid. Further each $R^6$ may each independently be straight chain or branched e.g. as derived from iso-stearic acid, and saturated as derived from lauric, palmitic, stearic or iso-stearic acids; or unsaturated as derived from oleic, linoleic or palmitoleic acids.

The index m represents the average number of repeat units in the oligomeric ester part of the molecule. Typically m will be at least 1 and desirably at least 1.5, though not usually more than 20 and desirably not more than 10 and will desirably be from 1.5 to 8. As the number is an average, m may be non-integral.

The properties of the compounds of the invention, particularly the HLB can be varied by choice of the hydrophilic and hydrophobic components of the molecules. Thus increasing the length of the alk(en)yl group $R^3/R^4$ and/or the group $R^6$ when these are hydrocarbyl, will give a more hydrophobic product; and increasing the number of free hydroxyl groups in the group $R^2$, generally linked with increasing length of the $R^2$ chain, or the use of disaccharide derivatives, and low levels or the absence of further esterification with fatty acids, will increase the hydrophilicity of the compounds of the formula (I). Where the compounds of the formula (I) have a free carboxyl group, then they may have anionic surfactant properties as well as non-ionic properties, especially under alkaline conditions (though being polyesters alkaline conditions may lead to some hydrolysis).

The properties of the products may also be varied by the inclusion of diols or non ASA diacids as described above. Including diols will generally make the products less hydrophilic, and because relatively more hydrophilic compounds are generally desirable the proportion of diol will usually be low. Including non-ASA diacids will generally make the products less hydrophobic (usually more hydrophilic) and accordingly relatively large amounts of such other diacid may be used. Particularly where the oligomeric chains are (on average) relatively short the inclusion of relatively large proportions of non-ASA diacids may effectively give a product which is a mixture of compounds including ASA residues and compounds not including such residues. As a corollary, deliberately mixing separately manufactured oligoesters made using ASAs and oligoesters made using non-ASA diacids may also be used to give products having a desired degree of hydrophilicty.

The oligomeric chain in the compounds of the invention will generally mean that they have a higher molecular weight and size as compared with e.g. alcohol ethoxylate surfactants. This may lead to useful properties as stabilisers at interfaces e.g. oil water interfaces, as in emulsions, because the molecules will be less easy to displace from the interface.

The compounds of the invention and particularly of the formula (I) can be made by reacting a polyol with an alk(en)yl dicarboxylic acid or, and more usually, anhydride, or other reactive derivative e.g. a lower alkyl diester. Where additional esterification is desired then this will usually be done either by subsequent reaction of the product of the above reaction with a fatty acid (or a mixture) or reactive derivative, or by carrying out a single stage reaction between polyol; alk(en)yl dicarboxylic acid, anhydride, or other reactive derivative; and fatty acid (or mixture), or reactive derivative.

The invention accordingly includes a method of making a surfactant compound of the invention which comprises reacting a polyol with an alk(en)yl succinic acid, anhydride or other reactive derivative, under esterification conditions to form an oligomeric oligoester of the invention. Optionally, simultaneously, subsequently or prior to the reaction forming the oligoester chain, a fatty acid may be included or reacted on to a relatively small proportion of the polyol OH groups to provide the further esterified products of the invention.

The invention particularly includes a method of making a compound of the formula (I) as defined above which comprises reacting a precursor polyol with an alk(en)yl succinic acid, anhydride or other reactive derivative, optionally additionally including a fatty acid, under esterification conditions to form a surfactant of the formula (I).

We have found that although it is not necessary to use a separate catalyst (the acid groups in the starting materials will provide some catalysis) the use of a catalyst (see below) will usually be beneficial. In particular, where alk(en)yl succinic anhydrides as such are used as the reagent, the initial esterification does not require a catalyst, merely warming the reagent together will generally lead to initial reaction. The subsequent further esterification stage will generally need higher temperatures and benefits from the use of a catalyst (see below).

Especially where the polyol (II) has four or more carbon atoms and four or more hydroxyl groups, usually two primary hydroxyls and 2 or more secondary hydroxyls, it may be susceptible to react to form cyclic ethers. For example sorbitol can form sorbitan cyclic ethers which may react further to form the Bicyclic diether iso-sorbide. This reduces the number of free hydroxyl groups and is thus generally undesirable, but may need to be taken into account in choosing the proportions of starting materials for making the oligoesters.

We have found that it is practical to make the compounds of the formula (I), under alkali catalysis, particularly alkali metal e.g. sodium or potassium, hydroxides or carbonates. Where further esterification is carried out, additional catalyst may be added between the first and second esterification stages if desired.

Desirably the esterification conditions include:

a the use of an alkali catalyst, particularly an alkali metal hydroxide and/or carbonate; and/or b a reaction temperature of from 100° C. to 200° C., more usually from 120° C. to 185° C. and desirably from 150° C. to 180° C., e.g. about 170° C.; and/or c a reaction pressure which is subambient, particularly from 50 to 250 mBar (0.5 to 25 kPa) e.g. about 100 mBar (10 kPa).

In these reactions carboxylic acid functionality may be provided by free carboxylic acids or by reactive derivatives such as anhydrides or by lower e.g. $C_1$ to $C_6$, alkyl, particularly methyl or ethyl, esters, as in ASA dialkyl esters. Where esters are used as the ASA source, the catalyst used may be an alkali as described above or a catalyst specifically for transesterification reactions e.g. titanate ester, such as tetrabutyl titanate.

Particularly where the polyol used in making the oligoester intermediate has more than 3 hydroxyl groups e.g. where it has five or more hydroxyl groups, particularly on adjacent carbon atoms, the polyol may be liable to react such as by cyclising e.g. to form sorbitan from sorbitol, or pyrolysis, if heated sufficiently. Thus, when these materials are used, it may be desirable to use temperatures that are lower than are typically in making carboxylic acid esters, particularly with relatively long chain acids. Typically, using such materials, the temperatures used will be at least 100° C., more usually at least 120° C. and desirably at least 150° C., but not more than 200° C., more usually not more than 185° C., particularly not more than 180° C., with reaction temperatures about 170° C., being particularly suitable. The use of mildly subambient pressure e.g. from 50 to 250 mBar (0.5 to 25 kPa) e.g. about 100 mBar (10 kPa) can benefit reaction speed to aid use of such temperatures.

If the materials produced by the synthesis are coloured, particularly by coloured impurities, then the level of colour may be reduced by treatment with activated carbon and/or by bleaching e.g. with hydrogen peroxide particularly in making products for personal care end use applications.

The compounds of this invention can be made to have a range of water and/or oil solubility and thus can be used as surfactants in water or oil based systems. In particular, the compounds of the invention may have HLB values in the range 4 to 18, including the relatively hydrophilic range 8 to 18 and the relatively oleophilic (hydrophobic) range 4 to 6.

Surfactants used in water based systems are generally water soluble, having an HLB greater than 7, particularly from 8 to 18. Such materials can be used as oil in water emulsifiers, particularly in personal care applications; as dispersants for pigments; as emulsifiers in emulsion polymerisation; as wetting agents in aqueous systems; as surfactants in domestic detergents, particularly in laundry formulations; in crop protection formulations particularly as adjuvants, dispersants and/or emulsifiers in agrochemical formulations; and other applications.

The properties of the surfactants of this invention also make them suitable as emulsifiers particularly in oil in water emulsions e.g. in personal care applications. Personal care emulsion products can take the form of creams and milks desirably and typically include emulsifier to aid formation and stability of the emulsion. Typically, personal care emulsion products use emulsifiers (including emulsion stabilisers) in amounts of about 3 to about 5% by weight of the emulsion.

The oil phase of such emulsions are typically emollient oils of the type used in personal care or cosmetic products, which are oily materials which is liquid at ambient temperature or solid at ambient temperature, in bulk usually being a waxy solid, provided it is liquid at an elevated temperature, typically up to 100° C. more usually about 80° C., so such solid emollients desirably have melting temperatures less than 100° C., and usually less than 70° C., at which it can be included in and emulsified in the composition.

The concentration of the oil phase may vary widely and the amount of oil is typically from 1 to 90%, usually 3 to 60%, more usually 5 to 40%, particularly 8 to 20%, and especially 10 to 15% by weight of the total emulsion. The amount of water (or polyol, e.g. glycerine) present in the emulsion is typically greater than 5%, usually from 30 to 90%, more usually 50 to 90%, particularly 70 to 85%, and especially 75 to 80% by weight of the total composition. The amount of surfactant used on such emulsions is typically from 0.1 to 10%, more usually 0.5 to 8%, more desirably 1 to 7%, particularly 1.5 to 6%, and especially 2 to 5.5%, by weight of the emulsion.

The end uses formulations of such emulsions include moisturizers, sunscreens, after sun products, body butters, gel creams, high perfume containing products, perfume creams, baby care products, hair conditioners, skin toning and skin whitening products, water-free products, anti-perspirant and deodorant products, tanning products, cleansers, 2-in-1 foaming emulsions, multiple emulsions, preservative free products, emulsifier free products, mild formulations, scrub formulations e.g. containing solid beads, silicone in water formulations, pigment containing products, sprayable emulsions, colour cosmetics, conditioners, shower products, foaming emulsions, make-up remover, eye make-up remover, and wipes. A preferred formulation type is a sunscreen containing one or more organic sunscreens and/or inorganic sunscreens such as metal oxides, but desirably includes at least one particulate titanium dioxide and/or zinc oxide, The surfactants of this invention can be used as emulsifiers in emulsion polymerisation. Typically emulsion polymerisation is carried out on emulsions of ethylenically unsaturated monomers in water. Suitable monomers include unsaturated carboxylic acids and their alkyl esters, amides, N-substituted amides and nitriles, aromatic vinyl compounds, diene compounds which may be included as monomers or specifically as crosslinking agents, vinylethers, vinylesters, olefines and hydrophobic allyl compounds.

Such emulsion polymerisation methods are particularly applicable to the manufacture of acrylic copolymers, for example those where at least 50%, more usually at least 60%, desirably at least 80% e.g. 90% or more up to 100%, by weight of the monomers are acrylic monomers. The acrylic polymers may be those based on mixed alkyl acrylates, especially where the predominant monomer is methyl methacrylate, and may include anionic units such as (meth)acrylic acid units or cationic units such as amino substituted ethylenically unsaturated monomers.

The amount of surfactant used will depend on the particular monomers and the polymerisation system used, the degree of colloidal stability needed and the desired particle size of the polymer in the product latex. For an otherwise conventional oil in water emulsion polymerisation, to give a latex having a particle size of from 80 to 500 nm the amount of surfactant used will typically be from 0.25 to 5 parts by weight surfactant per 100 parts by weight total monomer (phm). More usually the amount will be from 0.5 to 2.5 phm, particularly from 1 to 2 phm.

In microemulsion polymerisation systems, the concentration of monomer is typically substantially lower than in conventional emulsion or other dispersion polymerisation systems e.g. from 3 to 10% by weight. The proportion of surfactant relative to the amount of monomer is also relatively high because the microemulsion has higher interface area per unit mass of monomer corresponding to the smaller emulsion particle size and typical levels can be from 10 to 150 phm. Overall solids contents of microemulsion systems are usually in the range 15 to 30% by weight of the total emulsion.

The surfactants of this invention can be used as dispersants for solids in aqueous media, particularly for pigments, including inorganic pigments e.g. titanium dioxide, pigmentary iron oxide and organic pigments e.g. phthalocyanine pigments, carbon black, and similar materials. The amount of surfactant used in such dispersant applications depends on the materials employed and the dispersion concentration required, but is usually from 0.2 to 10% by weight of the solid e.g. pigment being dispersed. In aqueous dispersions, for inorganic pigments the amount used is typically from 0.05 to 5%, more usually 0.1 to 2.5%, by weight of the solid dispersed and for organic pigments typically the amount used is from 3 to 10% by weight of the solid dispersed. Typical such dispersions will contain up to about 70%, often up to about 65%, of inorganic pigment and up to about 35% by weight organic pigment, but this may be up to 50% for pigment pastes. When incorporated into end use products such as paints typical pigment levels in the final product will be about 3 to about 30%, particularly about 20 to about 25%, for inorganic pigments, about 1 to about 15% for organic pigments, particularly about 10 to about 12%, especially for phthalocyanine type organic pigments, and about 0.5 to about 5%, particularly about 3 to about 3%, for carbon black. The continuous phase in such dispersions will usually be water based.

The surfactants can also be used as domestic detergents for example in laundry applications and may be used alone or in combination with other, non-ionic, anionic, cationic, amphoteric and/or zwitterionic surfactants. Formulations including surfactants of this invention for laundry use will typically also include further components including one or more of builders e.g. phosphates, particularly sodium tripolyphosphate; organics such as citrate and/or tartrate; and/or zeolites; flow and/or filter aids, commonly used in powder formulations, which may include co-builders such as sodium carbonate and/or bicarbonate, particularly in powders where the builder is a zeolite (though because typical co-builders are alkali, they will not usually be used in hand washing formulations); corrosion inhibitors; anti-redeposition aids such as carboxy methyl cellulose; and optical brighteners. Further components may include perfumes; enzymes, including lipases, proteases, cellulases and/or amylases; bleaches, typically based on sodium perborate, sodium percarbonate or similar materials, which will typically be used with bleach activators such as tetra-acetyl ethylene diamine (TAED); and stabilisers such as phosphonates or ethylene diamine tetra-acetic acid (EDTA) usually as the sodium salt; soaps; foam control agents (often soaps) and fabric conditioners (softeners) such as quaternary ammonium salts and amine oxides which may be coated onto bentonite type clays.

The compounds of the invention can used as surfactants in agrochemical formulations, in particular as adjuvants for example with herbicides, fungicides, insecticides, acaricides and plant growth regulator formulations, dispersants and/or emulsifiers. The amount of surfactant used to disperse agrochemical(s), is typically at a concentration of 1 to 30% based on the formulation and used as adjuvants, a concentration of from 5 to 60% based on concentrate formulations and 1 to 100% in or as components for addition to tankmixes. Other conventional components can be included in such formulations such as oils e.g. mineral oil(s), vegetable oil(s) and alkylated vegetable oil(s); solvents and/or diluents; and other surfactants which may be anionic surfactants, cationic surfactants or non-ionic surfactants. Such other components will, as with formulations using purely conventional surfactants, be used in amounts based on the desired effect.

The surfactants of the invention can also be used in oilfield applications e.g. as foaming agents in foam drilling, as kinetic gas hydrate inhibitors and as water based drilling fluid lubricants.

Foam drilling fluids are water based drilling fluids in which the water phase is foamed e.g. to minimise formation damage of water sensitive formations. As foaming agents in foam drilling fluids the amount of the surfactant used will typically be from 1 to 3%, more usually from 1 to 2%, by weight of the drilling fluid.

Kinetic gas hydrate inhibitors are materials added to water containing hydrocarbon, particularly $C_1$ to $C_4$ hydrocarbon alkane containing streams to slow down gas hydrate formation or to modify the crystal form of the gas hydrate so as to reduce crystal agglomeration which otherwise would lead to pipe or similar blockage. In gas hydrate inhibition, the surfactants will typically be used at from 0.05 to 5% by weight based on the water phase of the stream being treated.

The surfactant compounds of the invention may be used to provide enhanced lubricity in water based drilling fluids. In use in this application the amount of surfactant used will typically be from 0.05 to 10% by weight of the fluid.

Surfactants used in oil based systems are generally oil soluble and usually water insoluble and in particular having an HLB of less than 7, more usually from 4 to 6. Such materials can be used as emulsifiers and/or stabilisers for water in oil emulsions; or as dispersants for solids in non-aqueous liquids. As such they can be used in a wide variety of applications including in: (water in oil) emulsion polymerisations, particularly to make polyacrylamide (PAM) or related polymers by free radical inverse emulsion polymerisation (i-PAM); emulsion explosives; in water in oil cosmetic emulsions; agrochemical, particularly plant growth regulator, herbicide, and/or pesticide, emulsions dispersions and suspoemulsions; and as emulsifiers and/or dispersants; dispersions of solids, such as pigments and/or inert inorganic metal salts, especially in organic media; oilfield drilling fluid additives, particularly as dispersants and/or emulsifiers for drilling muds and invert emulsion drilling fluids; metal working applications particularly in rolling oil emulsions and cutting fluids.

The surfactants of the invention can be used as emulsifiers in i-PAM polymerisation, in which acrylamide and any co-monomer(s), are dissolved in water, this solution is emulsified in oil, using surfactants as emulsifiers and stabilisers, and the polymerisation initiated. The result is a dispersion of water droplets, containing dissolved PAM, in the oil. Although the viscosity of the aqueous PAM solution is high, the effective viscosity of the emulsion is determined primarily by the oil continuous phase, chosen to be suitably low. In use e.g. in water treatment, the emulsion has to be broken, usually by inverting on dilution into water. The surfactant system must provide adequate emulsion stability before, during and after (for storage) polymerisation, but permit ready breaking of the emulsion during inversion on dilution into water, to facilitate rapid release of the polyacrylamide polymer into the water phase in which it will act. Inversion is commonly promoted by the addition of hydrophilic surfactants after the polymerisation. Relatively oleophilic surfactants of the invention can be used to emulsify and/or stabilise the water in oil emulsion used in this type of polymerisation process.

In i-PAM, the oil phase is typically a mineral oil, particularly a paraffin oil, or an ester oil and the amount of emulsifier surfactant used is typically from 2.5 to 7%, usually from 3 to 4%, by weight of the polymerisation emulsion. The emulsifier system will typically combine a polymeric surfactant, particularly including a surfactant of invention especially of the formula (I), and a low molecular weigh low HLB surfactant (relatively less effective as an emulsion stabiliser so that the stabilisation of the emulsion is not so good that inversion is difficult)—the low molecular weight enables it to readily diffuse away from the phase interface during inversion. Commonly the low molecular weight surfactants are fatty acid monoglycerides, fatty acid sorbitan esters or similar surfactants. The relative proportions by weight of polymeric surfactant to low HLB low molecular weight surfactant is typically from 5:95 to 50:50 more usually from 10:90 to 40:60 and commonly about 15:85 to 30:70.

Oleophilic types of surfactants of this invention can also be used in dispersing solids, particularly pigments such as those described above, in non-aqueous media such as white spirit or aromatic media. In such uses the amount of surfactant used will typically be from 0.5 to 7.5%, more usually from 1 to 5%, by weight of the dispersion.

The compounds of the invention are also useful as emulsifiers or emulsion stabilisers in emulsion explosives in which an oxidiser, typically an aqueous solution of an oxidiser salt usually nitrates, is emulsified in a liquid fuel, typically a hydrocarbon fuel such as mineral and/or paraffin oil, which may also include other petroleum components e.g. microcrystalline wax, paraffin wax, slack wax, and/or petroleum refining distillation residues. The oxidiser solution is usually a saturated or supersaturated aqueous solution, of nitrate salts, particularly $NH_4NO_3$, alkali metal nitrates or alkaline earth metal nitrates, optionally with minor proportions of other salts e.g. $NH_4Cl$ and typically contains 40% to 70% by weight ammonium nitrate and 20% of other nitrates. The internal oxidiser phase is typically at least 75% more usually more than 90% e.g. about 95%, by volume of the emulsion explosive. For use, emulsion explosives typically also include additives to sensitise the compositions to detonation. Commonly this is done by adding materials that provide solid surfaces e.g. solid $NH_4NO_3$, especially as prills, or gas filled voids e.g. by including sodium nitrite, which produces gas by chemical reaction, or glass microspheres, which provide physical voids.

The compounds of the invention particularly of the formula (I) can be used as emulsifiers alone or in combination with other typically oil soluble emulsifiers particularly sorbitan fatty acid esters such as sorbitan mono oleate (SMO); phospholipids such as soyalecithin or oxazoline or imidazoline derivatives thereof; PIBSA alkanolamine reaction products; or fatty acid condensation products with polyethylene glycols. The total amount of emulsifier used in emulsion explosives is typically from 0.5 to 5%, more usually from 1 to 4%, by weight based on the overall emulsion. Desirably, the proportion of emulsifier of the formula (I) is at least 50%, more usually at least 75%, by weight of the total emulsifier used in the emulsion explosive.

The compounds of the invention can be used as water in oil dispersants and/or emulsifiers in personal care and cosmetic applications, in particular, in formulations including relatively high concentrations of solutes in a dispersed hydrophilic phase and in the manufacture of multiple emulsions. The oil phase used in this aspect of the invention is typically an emollient oil which may be liquid or solid at ambient temperature.

The discontinuous, usually aqueous, phase can be water or a water based liquid, or a hydrophile phase which can be a solution in water of the hydrophilic material or the discontinuous phase can, in certain cases, be a substantially water free liquid phase of the hydrophilic material. In such systems the surfactant of the invention is typically used in an amount of 0.5 to 5%, more usually from 1 to 2%, by weight of the total emulsion.

The surfactants of this invention can be used as emulsifiers and/or dispersants in agrochemical applications. The invention accordingly includes an agrochemical emulsion or dispersion, in which at least one surfactant compound of the invention, particularly of the formula (I), is included as an emulsifier or dispersant. Within this, more particularly the invention includes:

i an agrochemical emulsion including an agrochemically active material which is dissolved, dispersed or emulsified in a first liquid component, the first liquid component being emulsified in a second liquid component;

ii an agrochemical formulation including an agrochemically active material which is dissolved, dispersed or emulsified in a first liquid component, a second liquid component being emulsified in the first liquid component;

iii an agrochemical dispersion in which a solid component is dispersed in a liquid phase.

The agrochemically active material(s) included in the emulsions and/or dispersions in this aspect of the invention can include one or more plant growth regulators, herbicides, and/or pesticides, for example insecticides, fungicides, acaricides, nematocides, miticides, rodenticides, bactericides, molluscicides and bird repellants. Examples of classes of actives include: Herbicides: including water soluble, particularly non-selective, herbicides, particularly N-phosphonomethyl glycine herbicides e.g. Glyphosate and Sulfosate, and the glufosinate and bipyridyl types of non-selective herbicides, triazines, substituted ureas, sulphonyl ureas, pyridine carboxylic acids, aryloxy alkanoic acids, 2-(4-aryloxy-phenoxy)propionic acids, bis-carbamates; Fungicides: including thiocarbamates, particularly alkylenebis(dithiocarbamate)s, strobilurins, dicarboximides, benzimidazoles, azoles, inorganic fungicides; Insecticides including benzoyl ureas; and Acaricides including tetrazines.

Particular applications of the polymeric surfactants of the invention in agrochemicals include:

Concentrated emulsions which contain both aqueous and non-aqueous phases with the continuous phase usually being aqueous.

Oil in water agrochemical emulsions are generally non-transparent white emulsions which are applied after further dilution in the spray tank.

Water in oil emulsions which are generally non-transparent (white) emulsions and are typically commercialised as ready to use formulations, ultra low volume systems, and other specialty applications.

Dispersions, in an aqueous or oil based liquid, of solid components which commonly will be insoluble actives, particularly fungicides or herbicides, but may be non-agrochemically active insoluble solid components.

Suspoemulsions which are systems in which at least one liquid and at least one solid disperse phase is included in a continuous phase, which is usually aqueous.

Combination formulations, particularly concentrated dispersions in which the compounds of the formula (I) can be used as dispersants in formulations which combine agrochemicals having different physical forms or presentations in formulation and/or different activities.

In agrochemical compositions, the surfactants of the invention, particularly of the formula (I), can be used alone or in combination with other polymeric surfactants, but desirably, the proportion of surfactant of the invention, particularly of the formula (I), is at least 50%, more usually at least 75%, by weight of the total polymeric surfactant used as emulsifier and/or stabiliser and/or dispersant in the composition.

One area of practical importance in this aspect of the invention is sunfilters and sunscreens or other cosmetics containing sunfilter and/or sunscreen components. The sunfilters or sunscreens can be physical sunscreens such as those based on titanium dioxide e.g. ultra-fine titanium dioxide, or zinc oxide, which are understood to act by strongly scattering ultraviolet radiation, or chemical sunfilters or sunscreens such as compounds that absorb ultraviolet radiation, particularly UVB and UVA sunscreen agents. The amount of sunfilters and/or sunscreen used will depend on the properties of the materials used, but typically for physical sunscreens the amount will be 0.1% to 5%, more usually from 0.25 to 2.5%, by weight of the overall emulsion and for chemical sunfilters and/or sunscreens 0.05 to 3%, more usually from 0.1 to 1.5%, by weight of the overall emulsion. Depending on their nature the sunfilter and sunscreen components may be present in the generally aqueous discontinuous phase or in the oil continuous phase or in both phases. Particularly where the sunscreens is a physical sunscreen, the overall emulsion will be combined suspension and emulsion and these are commonly referred to as suspoemulsions (see further below).

Suspoemulsions are a further important area in this aspect of the invention. They are briefly referred to above in connection with sunscreens, but other solid components can be included such as pigments as are often included in make up cosmetics. When pigments are used, they may be pigments organic or inorganic and may be present in the oil phase, particularly for organic pigments and hydrophobic inorganic pigments, or in the present in the water phase, particularly for hydrophilic inorganic pigments, or in both phases, when used are typically present in concentrations of from 0.5 to 20% more usually from 1 to 10%, by weight of the emulsion.

Generally the amount of the compound of the formula (I) used in cosmetic compositions of this aspect of the invention is from 0.5 to 7%, more usually from 1 to 5%, by weight of the formulation. The compound of the formula (I) can be used alone or in combination with other polymeric emulsifiers, but desirably, the proportion of the compound of the formula (I) is at least 50%, more usually at least 75%, by weight of the total emulsifier used in stabilising the cosmetic emulsion.

The surfactant compounds of the invention may also be used as demulsifiers in oilfield applications. Demulsifiers are typically used to aid separation of water emulsified in the hydrocarbon phase of oils. In use as demulsifiers, the amount of surfactant used as a demulsifier will typically be from 1 to 500 ppm, particularly from 5 to 150 ppm, by weight of the oil stream.

The surfactant compounds of the invention may also be used as emulsifiers and/or lubricants in metal working applications particularly in rolling oil emulsions and cutting fluids.

The compounds of the invention can further be used as dispersants finely divided solids in non-aqueous fluids, particularly liquid organic media. Examples of such materials include pigments, particularly for paints and solvent inks; dyes including disperse dyes; magnetic metal oxides; extenders and fillers; optical brightening agents; and textile auxiliaries; solids for oil based and invert emulsion drilling muds; dirt and solid particles in dry cleaning fluids; and magnetic materials for magnetic recording media. The medium is typically an oil such as a hydrocarbon or A natural or synthetic ester oil, or a coating composition resin such as an alkyd resin, or special mixture of glycols typically used in the preparation of multi-purpose pigment pastes or pigment concentrates. Such dispersions typically contain from 5 to 95%, more usually from 10 to 60%, and especially from 20 to 50%, by weight of the solid, depending on the nature of the solid and the relative densities. The dispersion may be made by conventional method for making dispersions.

The following Examples illustrate the invention. All parts and percentages are by weight unless otherwise stated.

| Materials | |
|---|---|
| Polyols | |
| Pol3 | glycerol (100% active) |
| Pol5 | xylitol (100% active) |
| Pol3/C5 | glycerol:xylitol mixture (4:1 molar ratio) |
| Pol6 | sorbitol (100% active) |
| Alkenyl succinic anhydrides | |
| ASA12 | C12 alkenyl succinic anhydride |
| ASA18 | C18 alkenyl succinic anhydride |
| Other diacid reagents | |
| DA4 | succinic acid (used as anhydride) |
| DA5 | glutaric acid |
| DA6 | adipic acid |
| Catalysts | |
| Cat1 | $K_2CO_3$ |
| Cat2 | KOH |
| Cat3 | NaOH |
| Oils | |
| Oil1 | iso-hexadecane oil (Arlamol HD ex Uniqema) |

Test Methods

Acid Value (AV)—was measured by the method of ASTM D1980-87.

Emulsion Stability—was assessed on oil in water emulsions (1% w/w emulsifier, 20% w/w oil) prepared by weighing 158 g of demineralised water into a 400 ml tall form beaker, adding 2 g of test emulsifier and stirring the mixture using a magnetic flea and hotplate/stirrer at ambient temperature until completely dissolved. 40 g of Oil 1 were then added to the aqueous solution and the mixture homogenised using an Ultra Turrax T25 blender at 11000 rpm (ca 183 Hz) for 2 minutes. The resultant emulsion was transferred to two 50 ml volumetric cylinders, one of which was stored at ambient temperature (Amb) and the other in a hotbox at 50° C. The emulsion mean droplet size (in μm) of the stored samples was measured using a Coulter Multisizer II after 1 day (1D), 1 week (1W), and 1 month (1M).

Molecular weight—was estimated using on a Viscotek Evolution gel permeation chromatograph (gpc), using Viscogel GMHHR-L columns (exclusion limit ~20 k Da) and antioxidant stabilised tetrahydrofuran (THF) at 1.0 ml.min$^{-1}$ as the mobile phase, a Viscotek Model 302 refractive index detector at an operating temperature of 40° C. with calibration against polystyrene standards. The detector was. Samples were made as solutions of 50 mg product in 10 ml THF were filtered through a 0.45 μm PTFE syringe filter prior to injection. Where necessary, samples were made soluble in THF by acetylation using acetic anhydride.

SYNTHESIS EXAMPLES

Example SE1

Oligo(Sorbitol Dodecyl Succinate)

Anhydrous sorbitol (91.1 g; 0.5 mol), dodecenyl succinic anhydride (80.52 g; 0.30 mol) and potassium carbonate (5.18 g; 7.5 mol % based on sorbitol) were charged to a 250 ml round bottomed flask fitted with a propeller stirrer, side-arm water condenser and collection flask, vacuum pump, nitrogen sparge, thermometer (thermocouple) and an isomantle. The mixture was heated under stirring (300 rpm; 5 Hz) to 170° C. with a nitrogen sparge under a vacuum of 100 mbar (10 kPa). The reaction was stopped when the acid value fell below 5 mgKOH.g$^{-1}$ (after 4 hrs) and the solid product discharged. The structure of the product was confirmed using MALDI mass spectrometry and gpc.

Further similar oligopolyesters were made by the general method set out in Example SE1 but making changes to the starting materials or material proportions. Table SE1 below (including SE1 for completeness) sets out materials used in making the products together with some information on the properties of the products made. In this table, the molar % figures are based on the polyol used.

Using these methods the products were very similar to corresponding compounds made using the method of SE1 giving the products as solids. The products made and the conditions used are summarised in Table SE1 below.

Sodium chloride was includes in some samples is to investigate emulsion electrolyte stability. These emulsions were tested for stability as described above and the results are as set out in Table AE1 below.

TABLE AE1

| | | | Emulsion Stability (mean droplet size in μm) | | | | | |
|---|---|---|---|---|---|---|---|---|
| | | | 1D | | 1W | | 1M | |
| Ex No | SE No | Salt (wt %) | Amb | 50° C. | Amb | 50° C. | Amb | 50° C. |
| AE1.1 | SE3 | 0 | 9.2 | 9.1 | 9.1 | 9.2 | 9.0 | 9.1 |
| AE1.1a | | 3 | — | 7.9 | — | Br | — | Br |
| AE1.2 | SE4 | 0 | 8.9 | 8.7 | 8.8 | 8.8 | 8.8 | 8.8 |
| AE1.3 | SE5 | 0 | 8.0 | 8.0 | 8.0 | 8.0 | 8.0 | 8.0 |
| AE1.4 | SE2 | 0 | — | 11.2 | — | 11.6 | — | 11.3 |
| AE1.4a | | 3 | — | 11.0 | — | 11.1 | — | Br |
| AE1.5 | SE1 | 0 | — | 8.6 | — | 8.5 | — | 8.5 |
| AE1.6 | SE7 | 0 | — | 8.1 | — | 8.0 | — | 8.0 |
| AE1.6a | | 3 | — | 7.6 | — | Br | — | Br |
| AE1.7 | SE8 | 0 | — | 7.0 | — | 7.1 | — | 7.1 |
| AE1.8 | SE6 | 0 | — | 8.1 | — | 7.9 | — | 7.6 |
| AE1.8a | | 3 | — | 8.8 | — | Br | — | Br |
| AE1.9 | SE12 | 0 | — | 7.7 | — | 7.6 | — | 8.7 |
| AE1.9a | | 3 | — | 9.2 | — | Br | — | Br |
| AE1.10 | SE11 | 0 | — | 6.8 | — | Br | — | Br |
| AE1.11 | SE13 | 0 | — | 8.3 | — | 8.3 | — | 8.5 |
| AE1.12 | SE14 | 0 | — | 8.0 | — | 8.1 | — | 7.8 |

TABLE SE1

| | Polyol | | ASA | | Diacid | | | | |
|---|---|---|---|---|---|---|---|---|---|
| Ex No | Type | Mol | Type | mol % | Type | mol % | Cat | AV | Mw |
| SE1 | Pol6 | 1 | ASA12 | 0.6 | — | — | Cat1 | 5 | 1790 |
| SE2 | Pol6 | 1 | ASA12 | 0.06 | DA4 | 0.54 | Cat1 | 4.4 | 1330 |
| SE3 | Pol6 | 1 | ASA12 | 0.15 | DA4 | 0.45 | Cat1 | 5 | 1930 |
| SE4 | Pol6 | 1 | ASA12 | 0.3 | DA4 | 0.3 | Cat1 | 8.1 | 1640 |
| SE5 | Pol6 | 1 | ASA12 | 0.45 | DA4 | 0.15 | Cat1 | 7.3 | 1430 |
| SE6 | Pol6 | 1 | ASA12 | 0.06 | DA6 | 0.54 | Cat1 | 3.6 | 1840 |
| SE7 | Pol6 | 1 | ASA12 | 0.15 | DA6 | 0.45 | Cat1 | 4.1 | 1860 |
| SE8 | Pol6 | 1 | ASA12 | 0.45 | DA6 | 0.15 | Cat1 | 4.9 | 1560 |
| SE9 | Pol6 | 1 | ASA18 | 0.6 | — | — | Cat1 | 1.9 | |
| SE10 | Pol6 | 1 | ASA18 | 0.06 | DA4 | 0.54 | Cat1 | 14 | |
| SE11 | Pol6 | 1 | ASA18 | 0.06 | DA5 | 0.54 | Cat1 | 4.2 | 4090 |
| SE12 | Pol6 | 1 | ASA18 | 0.06 | DA6 | 0.54 | Cat1 | 4.3 | 4330 |
| SE13 | Pol6 | 1 | ASA18 | 0.15 | DA6 | 0.45 | Cat1 | 4 | |
| SE14 | Pol6 | 1 | ASA18 | 0.15 | DA6 | 0.45 | Cat3 | 2.9 | 4800 |
| SE15 | Pol5 | 1 | ASA18 | 0.6 | — | — | Cat2 | 5 | 2240 |
| SE16 | Pol3/5 | 0.8/0.2 | ASA18 | 0.6 | — | — | Cat2 | 4.7 | 3290 |
| SE17 | Pol3 | 1 | ASA18 | 0.6 | — | — | Cat2 | 1.8 | 6130 |
| SE18 | Pol3 | 1 | ASA18 | 0.15 | DA6 | 0.45 | Cat2 | 5 | 3070 |

Application Examples

Application Example AE1

Test oil in water emulsions were made up using the following general emulsion formulation:

| Material | amount (wt %) |
|---|---|
| surfactant | 1 |
| Oil 1 | 20 |
| salt (NaCl) | 0 or 3 |
| water | to 100 |

The invention claimed is:

1. An oligoester surfactant compound which includes residues of:
   i) a $C_8$ to $C_{30}$ alkenyl succinic anhydride, acid or reactive derivative;
   ii) a polyol having at least 3 OH groups; and
   iii) optionally, esterified residues of a fatty acid;
   wherein the oligoester surfactant compound comprises on average at least one free hydroxyl group per polyol residue.

2. An oligoester surfactant compound which is the reaction product of:
   i) a $C_8$ to $C_{30}$ alkenyl succinic anhydride, acid or reactive derivative;
   ii) a polyol having at least 3 OH groups; and
   iii) optionally a fatty monocarboxylic acid or a reactive derivative;

wherein the oligoester surfactant compound comprises on average at least one free hydroxyl group per polyol residue.

3. A compound as claimed in claim 1 wherein the polyol has from 4 to 6 carbon atoms and at least 4 hydroxyl groups.

4. A compound as claimed in claim 3 wherein the polyol is sorbitol, maltitol, isomaltitol, isomalt, or lactitol.

5. A compound as claimed in claim 1 of the formula (I)

$$R^1-[OR^2O(O)C.C(HR^3).(HR^4)C.C(O)]_m-R^5 \quad (I)$$

wherein:
R$^1$ is H, or a group R$^6$(O)C—;
each R$^2$ is independently a C$_3$ to C$_{10}$ hydrocarbyl group, having at least one hydroxyl group which is either substituent free or esterified with a fatty acid residue of the formula R$^{6'}$(O)C—, where R$^{6'}$ is independently as defined for R$^6$, or an alk(en)yl succinic terminated oligoester group of the formula —[O(O)C.C(HR$^{3'}$).(HR$^{4'}$)C.C(O)OR$^{2'}$]$_{m'}$—R$^{1'}$, where R$^{1'}$, R$^{2'}$, R$^{3'}$, R$^{4'}$, and m' are independently as defined for R$^1$, R$^2$, R$^{3'}$, R$^{4'}$, and m' respectively;
independently for each pair of groups R$^3$ and R$^4$ on adjacent carbon atoms, one is a C$_6$ to C$_{30}$ alkenyl or alkyl group and the other is hydrogen;
R$^5$ is —OH, —OM, wherein M is a salt forming metal, an amine or ammonium group, a group —OR$^7$, or a group —OR$^2$O—R$^7$;
R$^6$ is a C$_1$ to C$_{21}$ aliphatic hydrocarbyl group;
R$^7$ is H or a group —C(O)R$^6$ where R$^6$ is independently as defined above; and
m is from 1 to 20.

6. A compound as claimed in claim 5 which is:
a) a polyol ended binary co-oligomer of the formula (Ia):

$$H-[OR^2O(O)C.C(HR^3).(HR^4)C.C(O)]_m-OR^2O-H \quad (Ia)$$

where R$^2$, R$^3$, R$^4$ and m are as defined in formula (I); or
b) a fatty acid ester of the formula (Ib):

$$R^1-[OR^{2b}O(O)C.C(HR^3).(HR^4)C.C(O)]_m-(OR^{2b})_n-R^{5b} \quad (Ib)$$

where
each R$^3$, R$^4$ and m is independently as defined in formula (I);
each R$^{1b}$ and each R$^{5b}$ is independently —H, or a group each R$^{2b}$ is independently a group R$^2$ as defined in formula (I), or such a group esterified with one or more groups —C(O)R$^6$; where each R$^6$ is independently as defined in formula (I);
n is 0 or 1;
such that the compound includes an average of at least 0.1, group —C(O)R$^6$ and an average of at least 1 OH group;
or a mixture of two or more of the compounds (Ia) or (Ib).

7. A compound as claimed in claim 5 wherein the group R$^2$ contains from 1 to 6 free hydroxyl groups.

8. A compound as claimed in claim 7 wherein the group R$^2$ is a group of the formula: —(CH$_2$)$_{p1}$(CHOH)$_{p2}$(CH$_2$)$_{p3}$— wherein p1 and p3 are each independently from 1 to 3, and p2 is from 1 to 6.

9. The compound of claim 5, wherein the group R$^3$ is a group —(CH$_2$)$_n$— where n is from 2 to 10.

10. The compound of claim 5, wherein the index m is from 3 to 20.

11. A method of making a compound as claimed in claim 1 which comprises reacting an alkenyl succinic anhydride, acid or reactive derivative with a polyol having at least 3 free hydroxyl groups under esterification conditions.

12. An emulsion including a compound as claimed in claim 1 as an emulsifier.

13. An emulsion as claimed in claim 12 in the form of a oil in water personal care emulsion in which the disperse oil phase is an emollient oil or wax.

14. An emulsion as claimed in claim 13 in the form of a cream or a milk and including from 3 to 5% by weight of the emulsion of emulsifier and/or emulsion stabiliser.

15. A method of emulsion polymerisation in which an emulsion of one or more ethylenically unsaturated monomers in water emulsified with a compound as claimed in claim 1 is subjected to free radical polymerisation.

16. A dispersion of a solid in an aqueous medium including from 0.2 to 10% by weight of the solid of a compound as claimed in claim 1.

17. A laundry detergent formulation including a compound as claimed in claim 1.

18. An agrochemical formulation including a compound as claimed in claim 1 as an adjuvant, dispersant and/or emulsifier.

19. A foam drilling fluid including from 1 to 3% by weight of the drilling fluid of a compound as claimed in claim 1 as a foaming agent.

20. A method of inhibiting gas hydrate formation which comprises including in a water containing hydrocarbon stream subject to hydrate formation a compound as claimed in claim 1 as a gas hydrate inhibitor.

21. A water based drilling fluid including from 0.05 to 10% by weight of the drilling fluid of a compound as claimed in claim 1 as a lubricating agent.

22. A method of polymerising or copolymerising acrylamide in which acrylamide and any co-monomer(s), are dissolved in water, this solution is emulsified in oil, and the polymerisation initiated, in which a compound as claimed in claim 1 as an emulsifier.

23. A method as claimed in claim 22 wherein the amount of emulsifier used is from 2.5 to 7% by weight of the polymerisation emulsion.

24. A dispersion of a solid in a non-aqueous medium including from 0.5 to 7.5% by weight of the dispersion of a compound as claimed in claim 1.

25. An emulsion explosive comprising an emulsion of an aqueous solution of an oxidiser salt in a liquid fuel including from 0.5 to 5% by weight based on the overall emulsion of a compound as claimed in claim 1 as an emulsifier.

26. A personal care emulsion or dispersion comprising a continuous phase of an emollient oil having dispersed therein a water based liquid, or a hydrophile phase and including a compound as claimed in claim 1 as an emulsifier and/or dispersant.

27. A dispersion as claimed in claim 26 which includes one or more sunscreen component.

28. A method of demulsifying a stream containing water emulsified in oil comprising adding to the stream from 1 to 500 ppm by weight of the oil stream of a compound as claimed in claim 1 as a demulsifier.

29. A metal working fluid including a compound as claimed in claim 1 as an emulsifier and/or lubricant.

30. A method of making an oligoester which comprises reacting a polyol (or a reactive derivative) with an alk(en)yl succinic anhydride, acid or reactive derivative, under esterification conditions to form an oligoester.

* * * * *